US011714827B2

(12) United States Patent
Iglesias et al.

(10) Patent No.: US 11,714,827 B2
(45) **Date of Patent: *Aug. 1, 2023**

(54) AUTOMATED DYNAMIC CONTENT SCHEDULER

(71) Applicants: Marcos Alfonso Iglesias, Valley Park, MO (US); Elizabeth B. Goede, Scituate, MA (US)

(72) Inventors: Marcos Alfonso Iglesias, Valley Park, MO (US); Elizabeth B. Goede, Scituate, MA (US)

(73) Assignee: HARTFORD FIRE INSURANCE COMPANY, Hartford, CT (US)

( * ) Notice: Subject to any disclaimer, the term of this patent is extended or adjusted under 35 U.S.C. 154(b) by 89 days.

This patent is subject to a terminal disclaimer.

(21) Appl. No.: 17/444,712

(22) Filed: Aug. 9, 2021

(65) Prior Publication Data

US 2021/0365476 A1 Nov. 25, 2021

Related U.S. Application Data

(63) Continuation of application No. 16/881,506, filed on May 22, 2020, now Pat. No. 11,120,045, which is a continuation of application No. 14/967,750, filed on Dec. 14, 2015, now Pat. No. 10,956,441.

(51) Int. Cl.
*G06F 16/27* (2019.01)
*H04L 67/10* (2022.01)

(52) U.S. Cl.
CPC .............. *G06F 16/27* (2019.01); *H04L 67/10* (2013.01)

(58) Field of Classification Search
None
See application file for complete search history.

(56) References Cited

U.S. PATENT DOCUMENTS

2002/0069089 A1* 6/2002 Larkin .................. G16H 40/20 705/4
2002/0091552 A1* 7/2002 Dombroski ........... G06Q 30/02 705/4

(Continued)

*Primary Examiner* — Dawaune A Conyers
(74) *Attorney, Agent, or Firm* — Buckley, Maschoff & Talwalkar LLC

(57) ABSTRACT

According to some embodiments, a selection server is in communication with a potential communication device database and a currently participating device database, the potential communication device database storing information about communication devices associated with a transition from a first state to a second state, including at least one communication address associated with each communication device. The selection server may automatically identify a communication device as meeting a pre-determined criteria and copy information about the identified communication device from the potential communication device database to the currently participating device database.
A scheduling server may automatically schedule a series of communication events between a monitoring device and the identified communication device and arrange for a communication link to be established for each of the scheduled series of communication events until a transition from the second state back to the first state is detected for the identified communication device.

24 Claims, 12 Drawing Sheets

100
110 POTENTIAL COMMUNICATION DEVICE DB
142
SELECTION SERVER 140
120 CURRENTLY PARTICIPATING DEVICE DB
152
SCHEDULING SERVER 150
IDENTIFIED COMMUNICATION DEVICE 170
COMMUNICATION LINK
MONITORING DEVICE 160

(56) References Cited

U.S. PATENT DOCUMENTS

2005/0261957 A1* 11/2005 Fisher .................. G06Q 10/105
705/320
2014/0278830 A1* 9/2014 Gagne ............. G06Q 10/06398
705/7.42
2017/0132395 A1* 5/2017 Futch ..................... G06Q 40/08

* cited by examiner

900

| INJURED/ILL PERSON IDENTIFIER 902 | COMMUNICATION IDENTIFIER 904 | CURRENT WEEK 906 | CURRENT LEVEL OF FUNCTION 908 | LINK STATUS 910 |
|---|---|---|---|---|
| I_101 | (555) 555-5555 | 3 | 4 | CALL PENDING |
| I_102 | JOE@EMAIL.COM | 3 | 4 | CALL COMPLETED |
| I_103 | PORTAL USER NAME | 4 | 3 | CALL COMPLETED |
| I_104 | (555) 555-1234 | 4 | 2 | CALL COMPLETED |

| ILL OR INJURED INDIVIDUAL IDENTIFIER 1002 | COMMUNICATION IDENTIFIER 1004 | CURRENTLY SCHEDULED COMMUNICATION 1006 | NEXT SCHEDULED COMMUNICATION 1008 | PHYSICAL DELIVERY 1010 |
|---|---|---|---|---|
| III_101 | (555) 555-5555 | 3/2/2018 | 3/9/2018 | MOTIVATIONAL CD |
| III_102 | JOE@EMAIL.COM | 3/2/2018 | 3/9/2018 | STRESS BALL |
| III_103 | PORTAL USER NAME | 3/5/2018 | 3/12/2018 | NONE |
| III_104 | (555) 555-1234 | 3/5/2018 | 3/12/2018 | SLEEP MASK |

FIG. 10

AUTOMATED DYNAMIC CONTENT SCHEDULER

CROSS-REFERENCE TO RELATED APPLICATIONS

The present application is a continuation of U.S. patent application Ser. No. 16/881,506 entitled "AUTOMATED DYNAMIC CONTENT SCHEDULER" and filed on May 22, 2020 which was a continuation of U.S. patent application Ser. No. 14/967,750 entitled "AUTOMATED DYNAMIC CONTENT SCHEDULER" and filed on Dec. 14, 2015. The entire contents of those applications are incorporated herein by reference.

FIELD

The present invention relates to computer systems and more particularly to computer systems that are utilized in connection with automatically scheduling content.

BACKGROUND

In applications associated with distributed communication networks, it may be important to help facilitate and/or determine when one or more communication devices transition from a second state back into a first state. Such information can, for example, be used to take remedial steps to hasten the communication device's return to the first state and/or allow an enterprise to take other steps in anticipation of the communication device not returning to the first state in the near future. Facilitating a return to the first state, however, can be a time consuming and error prone task—especially when there are a substantial number of communication devices. It would therefore be desirable to provide systems and methods to facilitate a communication device's ability to transition back to a first state.

SUMMARY

A system is disclosed wherein a selection server is in communication with a potential communication device database and a currently participating device database, the potential communication device database storing information about communication devices associated with a transition from a first state to a second state, including at least one communication address associated with each communication device. The selection server may automatically identify a communication device as meeting a pre-determined criteria and copy information about the identified communication device from the potential communication device database to the currently participating device database. A scheduling server may automatically schedule a series of communication events between a monitoring device and the identified communication device and arrange for a communication link to be established for each of the scheduled series of communication events until a transition from the second state back to the first state is detected for the identified communication device.

By facilitating a communication device's ability to transition back to a first state, embodiments may provide improved data exchange over a distributed communication network.

With these and other advantages and features of the invention that will become hereinafter apparent, the invention may be more clearly understood by reference to the following detailed description of the invention, the appended claims, and the drawings attached hereto.

BRIEF DESCRIPTION OF THE DRAWINGS

FIG. 9 is a tabular portion of a currently participating device database that might be provided in accordance with some embodiments.

FIG. 10 is a tabular portion of a scheduled communication event database that might be provided in accordance with some embodiments.

DETAILED DESCRIPTION

The present invention provides significant technical improvements to facilitate a communication device's ability to transition back to a first state. The present invention is directed to more than merely a computer implementation of a routine or conventional activity previously known in the industry as it significantly advances the technical efficiency, access and/or accuracy of data created by devices described in connection with some embodiments by implementing a specific new method and system as defined herein. The present invention is a specific advancement in the areas of selection server, scheduling servers, and/or monitoring by providing technical benefits in data accuracy, data availability, data transparency, and data integrity and such advances are not merely a longstanding commercial practice. The present invention provides improvement beyond a mere generic computer implementation as it involves the processing and conversion of significant amounts of data in a new beneficial manner as well as the interaction of a variety of specialized back-end, client, and/or third-party systems, networks, and subsystems. For example, in the present invention information may be transmitted to automatically schedule communication links with identified communication devices, and such events may be facilitated as appropriate in an accurate and transparent manner.

Figure 1:
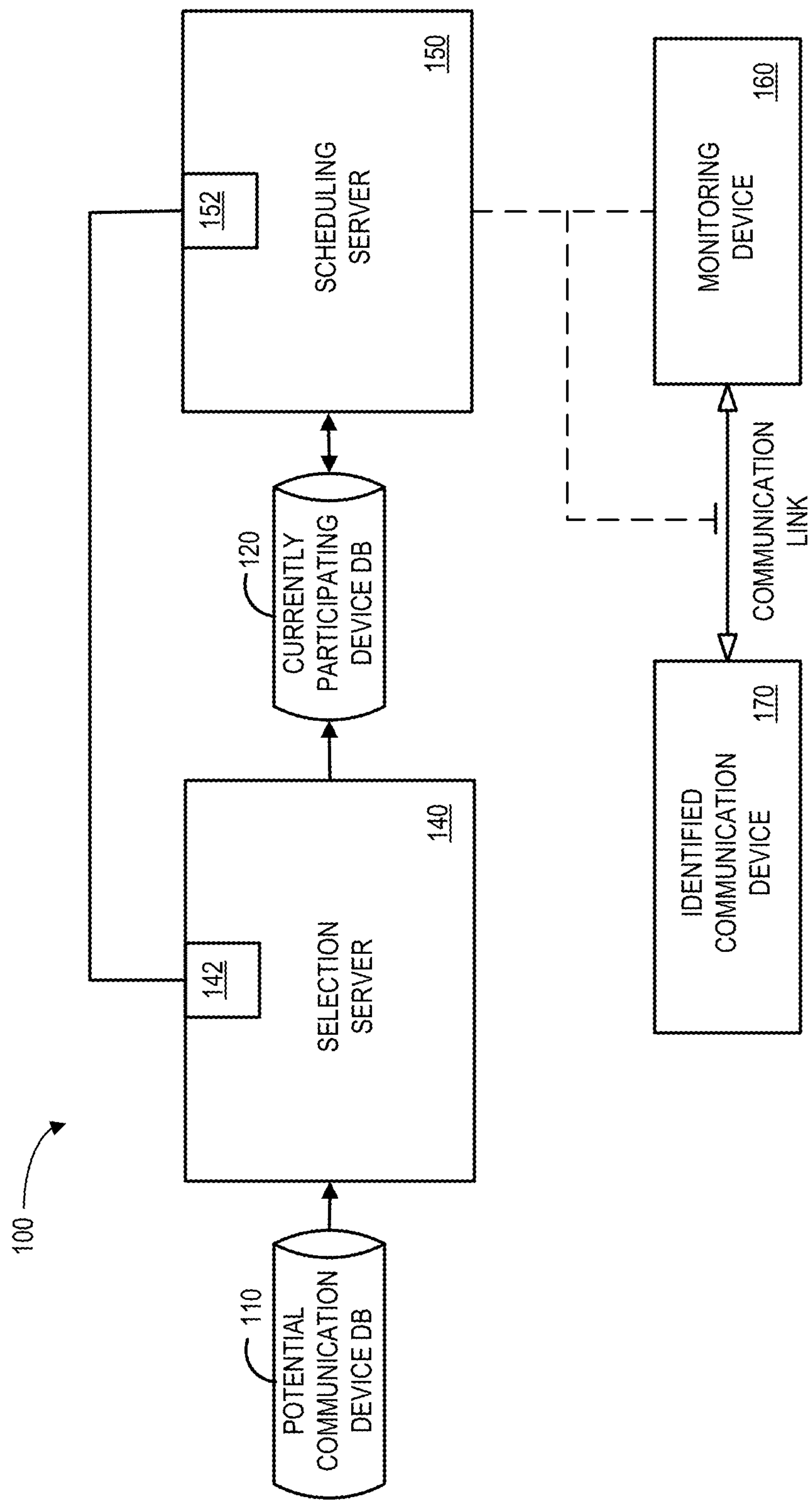
FIG. 1 is a high level block diagram that illustrates a system in accordance with some embodiments.

Some embodiments described herein may facilitate a communication device's ability to transition back to a first state. Further, some embodiments may provide a mechanism that automates an interface that might be used, for example, by operators and/or administrators of an enterprise computer server and/or a monitoring device. FIG. 1 is block diagram of a system 100 according to some embodiments of the present invention. In particular, the system 100 includes a selection server 140, coupled to a potential communication device database 110, that exchanges information with a scheduling server 150, either of which may store information into and/or retrieve information from currently participating device database 120.

The selection server 140 and/or scheduling server 150 might be, for example, associated with a Personal Computers ("PC"), a web portal, a laptop computer, an enterprise server, a server farm, and/or a database or similar storage devices. The selection server 140 and/or scheduling server 150 may, according to some embodiments, further include a rules engine and/or rendering component as described herein.

According to some embodiments, an "automated" selection server 140 and/or scheduling server 150 may help facilitate communications between a monitoring device 160 and an identified communication device 170 to facilitate a return to a first state by the identified communication device 170. For example, the selection server 140 and/or scheduling server 150 may automatically establish communication links between the monitoring device 160 and the identified communication device 170 (e.g., on a weekly basis). As used herein, the terms "automated" and "automatically" may refer to, for example, actions that can be performed with little (or no) intervention by a human.

As used herein, devices, including those associated with the selection server 140 and/or scheduling server 150 (or any other device described herein), may exchange information via any distributed communication network which may be one or more of a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

The selection server 140 and/or scheduling server 150 may store information into and/or retrieve information from the databases 110, 120. The databases 110, 120 might be locally stored or reside remote from the selection server 140 and/or scheduling server 150. According to some embodiments, the selection server 140 and/or scheduling server 150 exchanges information about information in the databases 110 120, such as by forwarding an electronic file or signal to an electronic transaction system, an electronic messaging communication server, and/or an external platform (e.g., a workflow management system, calendar application, etc.).

Note that the selection server 140 and scheduling server 150 might communicate via one or more communication ports 142, 152. Further note that these ports 142, 152 might comprise a single device, might provide electronic security measures for a distributed communication network (e.g., a firewall), and/or might provide load balancing services (e.g., arranging for multiple processors and/or programming instances to process information simultaneously) according to some embodiments.

Although a single selection server 140 and scheduling server 150 are shown in FIG. 1, any number of such devices may be included. Moreover, various devices described herein might be combined according to embodiments of the present invention. For example, in some embodiments, the selection server 140 and scheduling server 150 might be co-located and/or may comprise a single apparatus.

Figure 2:
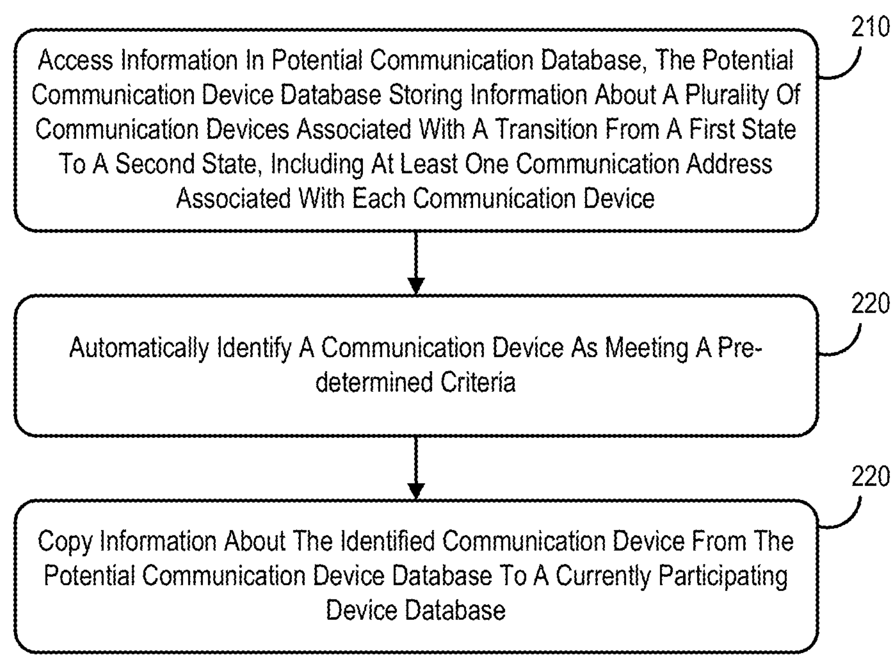
FIG. 2 is a flow chart that illustrates a selection server process that may be performed according to some embodiments.

FIG. 2 illustrates a method that might be performed, for example, by the selection server of the system 100 described with respect to FIG. 1 according to some embodiments. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At 210, a selection server, in communication with a potential communication device database and a currently participating device database, may access information in the potential communication database. The potential communication device database may, for example, store information about a plurality of communication devices associated with a transition from a first state to a second state, including at least one communication address associated with each communication device. As used herein, the phrase "communication device" might refer to, for example, a telephone, a personal computer, a smartphone, a smartwatch, a table computer, and/or a chat interface (e.g., adapted to exchange text, audio, and/or video messages).

At 220, the selection server may automatically identify a communication device as meeting a pre-determined criteria. For example, a sub-set of the communication devices might be identified as currently being in the second state and having characteristics indicating that a series of communication events with the communication device might encourage a transition back to the first state. At 230, the selection server may copy information about the identified communication device from the potential communication device database to the currently participating device database.

Figure 3:
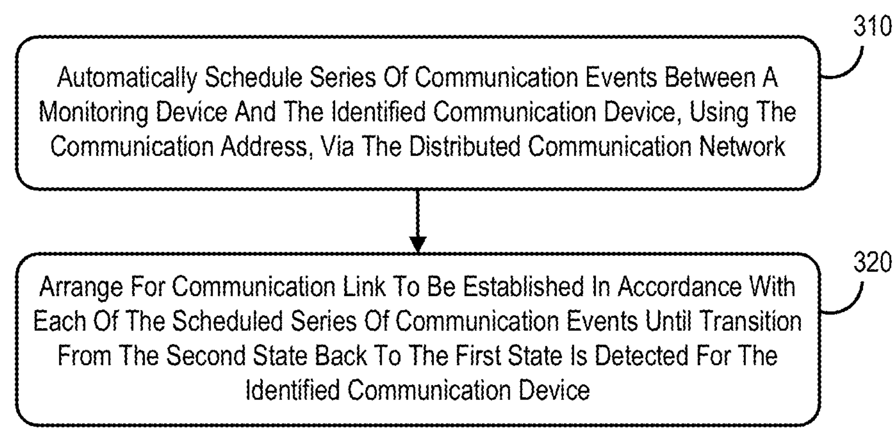
FIG. 3 is a flow chart that illustrates a scheduling server process that may be performed according to some embodiments.

FIG. 3 illustrates a method that might be performed, for example, by the scheduling server 150 of the system 100 described with respect to FIG. 1 according to some embodiments. At 310, the scheduling server (which may be coupled to the currently participating device database) might automatically schedule a series of communication events between a monitoring device and the identified communication device, using the communication address, via a distributed communication network (e.g., a PSTN, the Internet, and/or a web portal). At 320, the scheduling server may arrange for a communication link to be established in accordance with each of the scheduled series of communication events until a transition from the second state back to the first state is detected for the identified communication device. According to some embodiments, the scheduling server may also automatically arrange for a physical item to be delivered to a postal address associated with the communication device in connection with at least some of the scheduled series of communication events.

Figure 4:
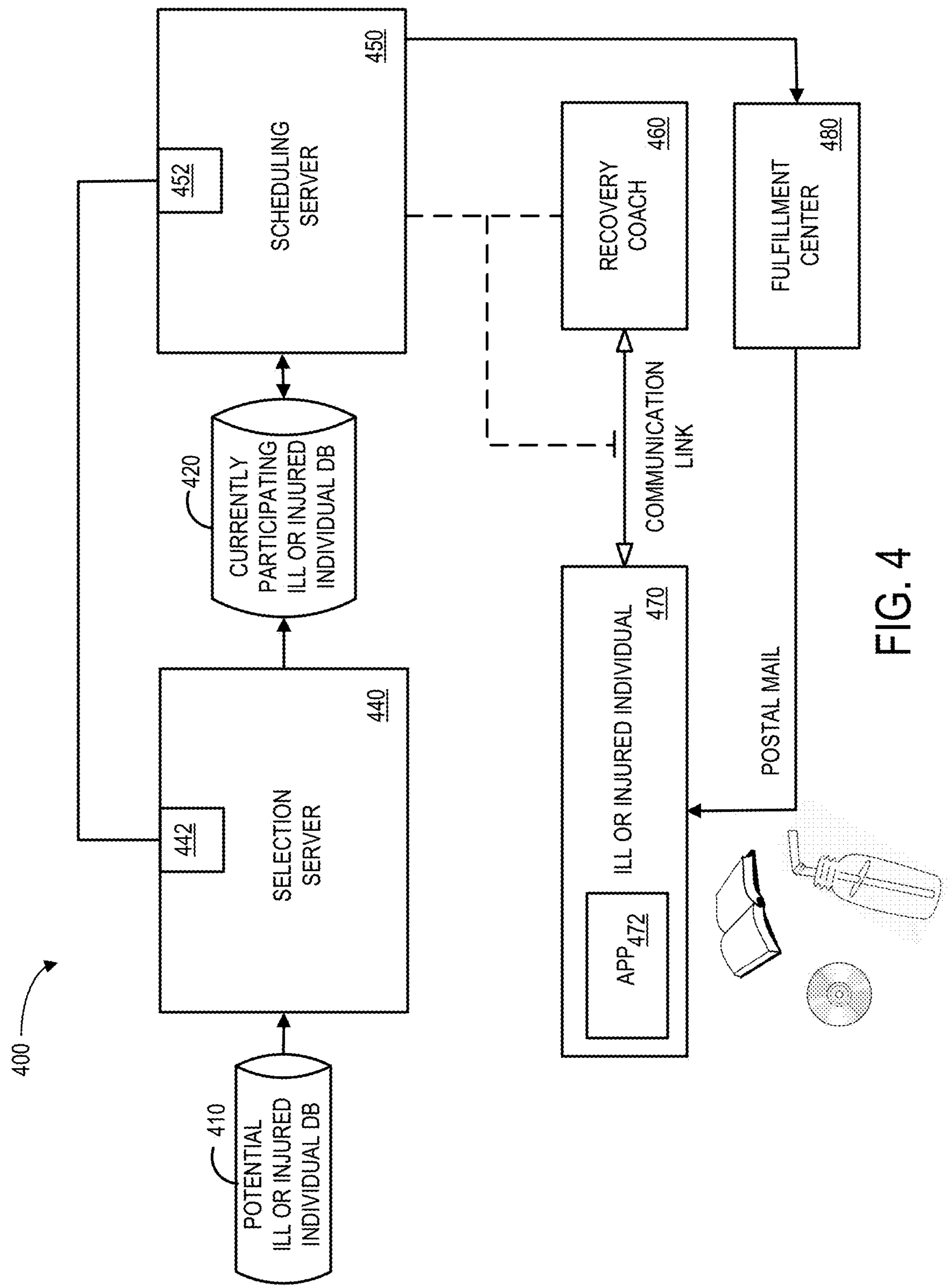
FIG. 4 is a block diagram that illustrates aspects of a computer system provided in accordance with some embodiments of the invention.

Some embodiments described herein might be associated with, for example, an ill or injured individual. The ill or injured individual might be associated with, for example, an injured worker (e.g., someone who is missing work due to illness or injury), workers' compensation insurance, group benefits insurance (e.g., short or long term disability insurance), automobile insurance, etc. For example, FIG. 4 is block diagram of a computer system 400 according to such embodiments of the present invention. As before, the system 400 includes a selection server 440, coupled to a potential ill or injured individual database 410, that exchanges information with a scheduling server 450, either of which may store information into and/or retrieve information from a currently participating ill or injured individual database 420.

The selection server 440 and/or scheduling server 450 might be, for example, associated with a PC, a web portal, a laptop computer, an enterprise server, a server farm, and/or a database or similar storage devices. The selection server 440 and/or scheduling server 450 may, according to some embodiments, further include a rules engine and/or rendering component as described herein.

According to some embodiments, an automated selection server 440 and/or scheduling server 450 may help facilitate communications between a monitoring device, such as a telephone associated with a recovery coach 460 (e.g., a return to work coach or other type of coach), and an identified communication device associated with an ill or injured individual 470 to facilitate a return to a "first state" (from a "second state") by the identified disabled individual 470. In this example, the first state is associated with an "at work" or "functional" status and the second state is associated with a "not at work" or "non-fully functional" status. Note that in some embodiments, at least one intermediate state may exist between the "at work" or "fully functional" and "not at work" or "non-fully functional" states, such as a "modified work duty" or "partially functional" state. The selection server 440 and/or scheduling server 450 may automatically establish communication links between the recovery coach 460 (e.g., a return to function coach) and the ill or injured individual 470 (e.g., on a weekly basis).

Note that the selection server 440 and scheduling server 450 might communicate via one or more communication ports 442, 452. Further note that these ports 442, 452 might comprise a single device, might provide electronic security measures for a distributed communication network (e.g., a firewall), and/or might provide load balancing services (e.g., arranging for multiple processors and/or programming instances to process information simultaneously) according to some embodiments.

Although a single selection server 440 and scheduling server 450 are shown in FIG. 4, any number of such devices may be included. Moreover, various devices described herein might be combined according to embodiments of the present invention. For example, in some embodiments, the selection server 440 and scheduling server 450 might be co-located and/or may comprise a single apparatus.

According to some embodiments, the selection server 440 may access information in the potential ill or injured individual database 410. The potential ill or injured individual database 410 may, for example, store information about a plurality of individuals associated with a transition from an "at work" to a "not at work" state or from a "fully functional" to "non-fully functional" state, including at least one communication address (e.g., telephone number, email address, etc.) associated with each individual.

The selection server 440 may automatically identify an ill or injured individual 470 as meeting a pre-determined criteria. For example, a sub-set of the ill or injured individuals might be identified as currently being "not at work" or "non-fully functional" and having characteristic indicating that a series of communication events with the disabled individual 470 might encourage a transition back to the "at work" or "fully functional" state. The pre-determined criteria might be associated with, for example, a geographic location (e.g., a recovery coach 460 might be more suitable in some US states as compared to other jurisdictions), a length of time in a "not at work" or "non-fully functional" status, a type of injury (e.g., a recovery coach 460 or return to function coach might be more suitable for individual's with back injuries as compared to other physical problems), whether or not the ill or injured individual's attorney approval may be required, a language spoken (e.g., does the ill or injured individual 470 speak English?), a "behavioral flag," and/or a risk score. As used herein, the phrase, "behavioral flag" or "behavioral characteristic" might refer to, for example, a "yellow flag" such as an expectation (e.g., the ill or injured individual 470 assumes he or she will not return to work or full functionality for longer than a predetermined threshold period of time, such as 10 days), a belief (e.g., that something must be seriously wrong), catastrophic thinking (e.g., that he or she will never return to work or full functionality—or some other worst-case scenario), fear (e.g., of re-injury or loss of income), perceived injustice (e.g., why did this have to happen to me?), passivity (e.g., an over-emphasis on what other parties will do for the ill or injured individual 470), and/or a lack of coping skills (e.g., managing time, goals, stress, anger, and/or sleep habits). Note than an increased presence of yellow flags may indicate that a particular ill or injured individual may find the recovery program especially helpful. The selection server 440 may then copy information about the identified ill or injured individual 470 from the potential ill or injured individual database 410 to the currently participating ill or injured individual database 420.

The scheduling server 450 might automatically schedule a series of communication events between a monitoring device associated with the recovery coach 460 and the identified ill or injured individual 470, using the communication address, via a distributed communication network (e.g., a PSTN, Internet, and/or web portal). The scheduling server 450 may arrange for a communication link to be established in accordance with each of the scheduled series of communication events until a transition from the "not at work" or "non-fully functional" state back to the "at work" or "fully functional" state is detected for the identified ill or injured individual 470. The recovery coach 460 might, for example, use the series of communications with the ill or injured individual to encourage physical activity, social activity, and/or cognitive activity. According to some embodiments, a software application 472 is associated with the communication device of the ill or injured individual 470. The software application 472 might include, for example, workbook materials, training media, activity tracking features, and/or goal tracking functionality.

According to some embodiments, the scheduling server 450 may also automatically arrange for a physical item to be delivered to a postal address or an electronic address associated with the ill or injured individual 470 in connection with at least some of the scheduled series of communication events. This might be arranged, for example, by transmitting one or more electronic records from the scheduling server 450 to a fulfilment center 480 adapted to facilitate such deliveries. By way of examples only, the scheduling server 450 might automatically arrange for a physical workbook to be delivered in connection with the first of the scheduled series of communication events. As other examples, the physical item might include an activity tracking device, a water bottle, a wrist band, a stress ball, a sleeping mask, a cap or visor, training media (e.g., a CD containing instructional material), and a certificate of completion (e.g., indicating that the ill or injured individual has successfully completely participating in the program). Note that the item delivered from to the ill or injured individual 470 might, according to some embodiments, comprise an electronic delivery of materials (e.g., an audio file might be downloaded to a smartphone associated with the ill or injured individual 470).

Figure 5:
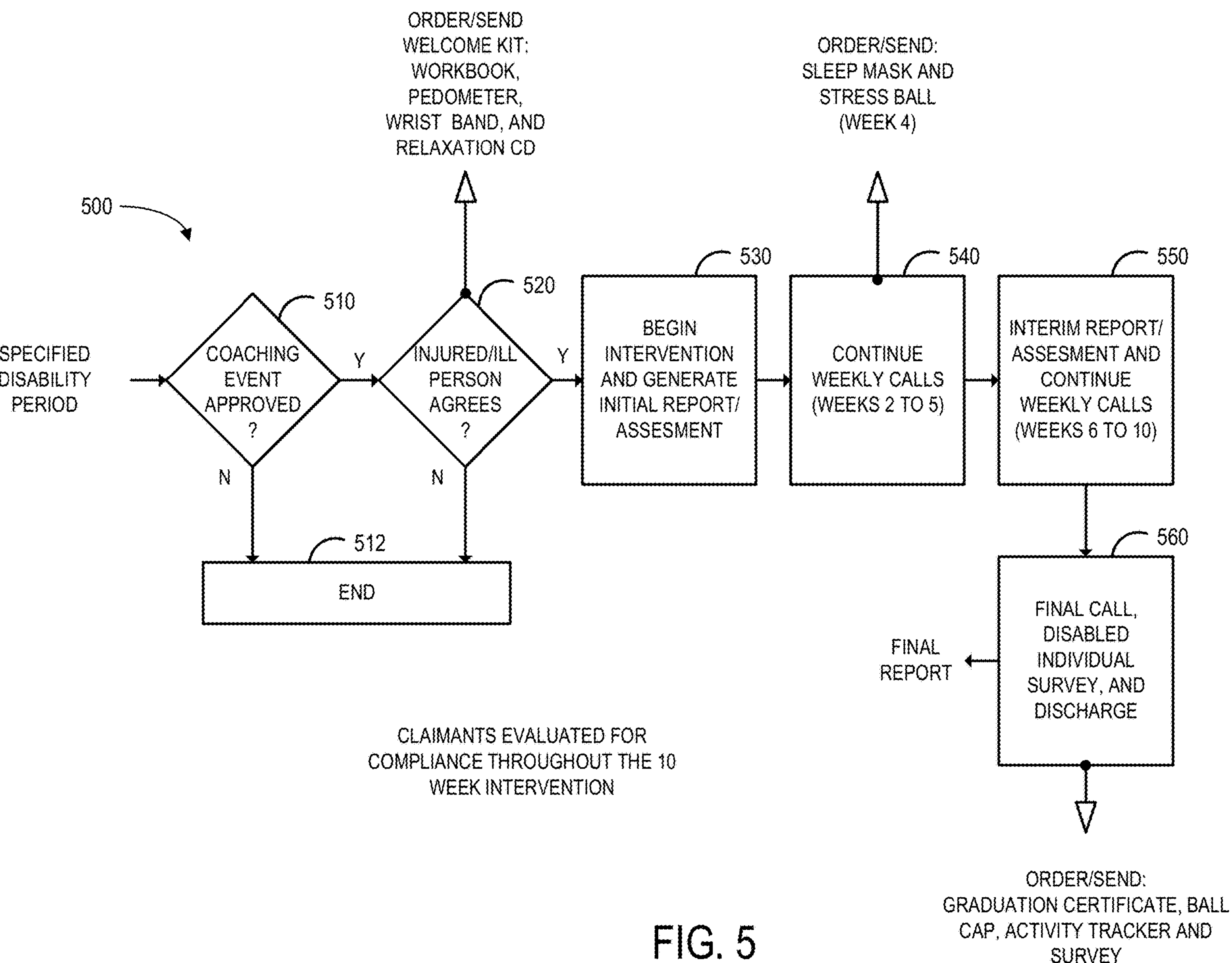
FIG. 5 is an information flow diagram illustrating a process that may be performed in accordance with some embodiments.

FIG. 5 is an information flow diagram illustrating a 10 week intervention process 500 that may be performed in accordance with some embodiments. The process 500 might be initiated, for example, after a pre-determined specified disability duration (e.g., 21 days of missed work). At 510, it may be determined if a coaching event is approved, such as by determining if the ill or injured individual meets one or more pre-determined criteria. If the event is not approved at 510, the process 500 ends at 512. If the event is approved at 510, it is determined if the ill or injured individual agrees to participate at 520. If the ill or injured individual does not agree to participate at 520, the process 500 ends at 512.

If the ill or injured individual agrees to participate at 520, a welcome kit may be mailed to the ill or injured individual (e.g., including a pedometer, wristband, and relaxation CD), the intervention may begin at 530 (e.g., at week 1), and an initial report and/or assessment may be generated. Weekly calls may be continued in weeks 2 through 10. According to some embodiments, other materials (e.g., a sleep mask and/or stress ball) might be mailed to the ill or injured individual during this time. At 550, an interim report or assessment may be generated and weekly calls may continue for weeks 6 through 10. A final call with the ill or injured individual may be made at 560, survey information may be collected, and the ill or injured individual may be discharged from the program with a final report. According to some embodiments, a graduation certificate, visor/baseball cap, activity tracker, and water bottle may also be mailed to the ill or injured individual at this point.

Figure 6:
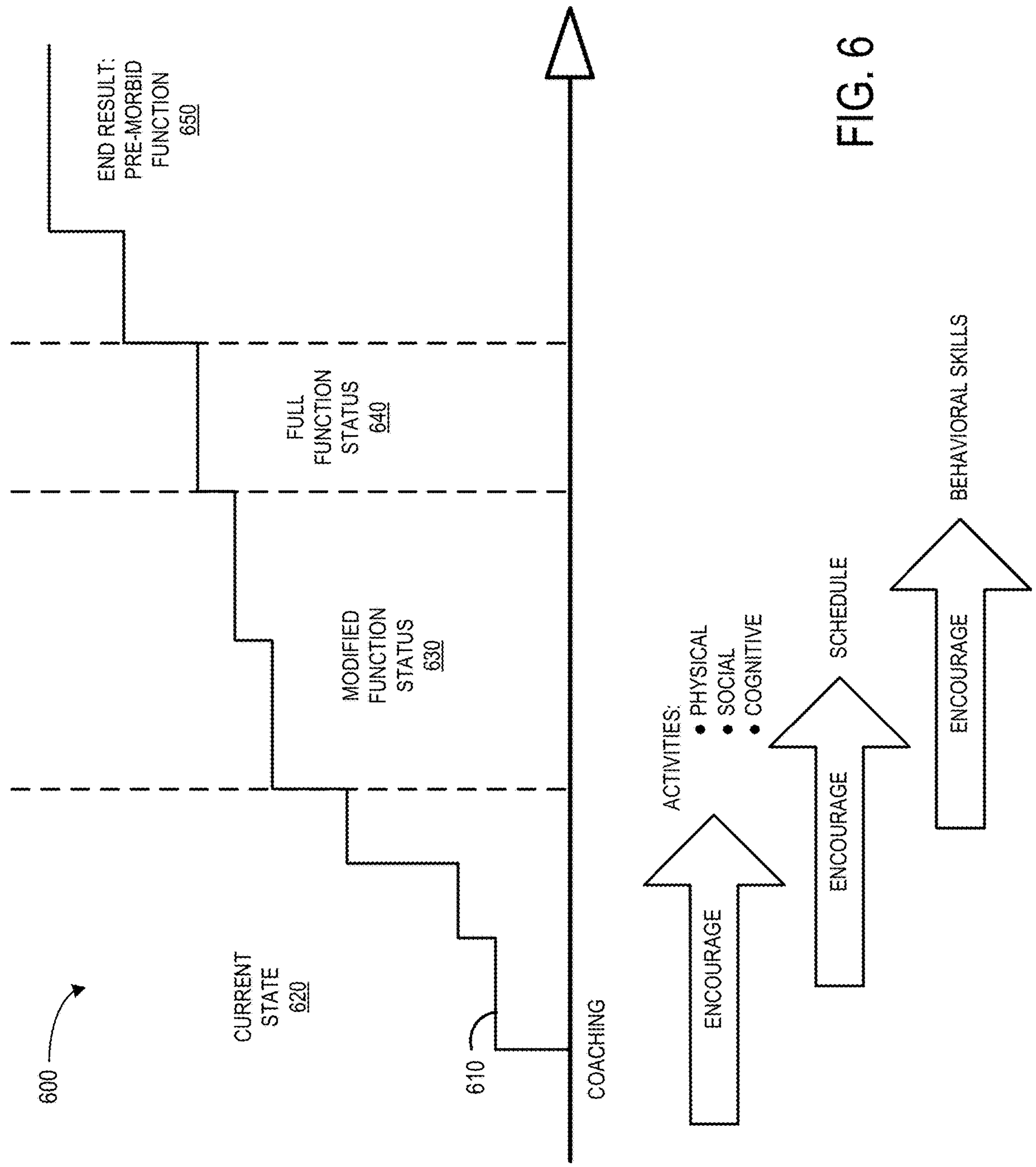
FIG. 6 illustrates an ill or injured individual's transition in according to some embodiments.

FIG. 6 illustrates an ill or injured individual's transition 600 in according to some embodiments. In particular, the ill or injured individual's level of activity 610 may transition from a current state 620 (not at work or non-fully functional), to a modified function status 630 (modified work state), to a full function status 640 (full work state), and—eventually, to an end result of a normal state 650 (fully functional work state or pre-morbid function status). During the transition, the recovery coach may encourage activities (e.g., physical, social, and/or cognitive activities), encourage and help with the ill or injured individual's schedule, and/or encourage and/or promote the ill or injured individual's behavioral skills.

Figure 7:
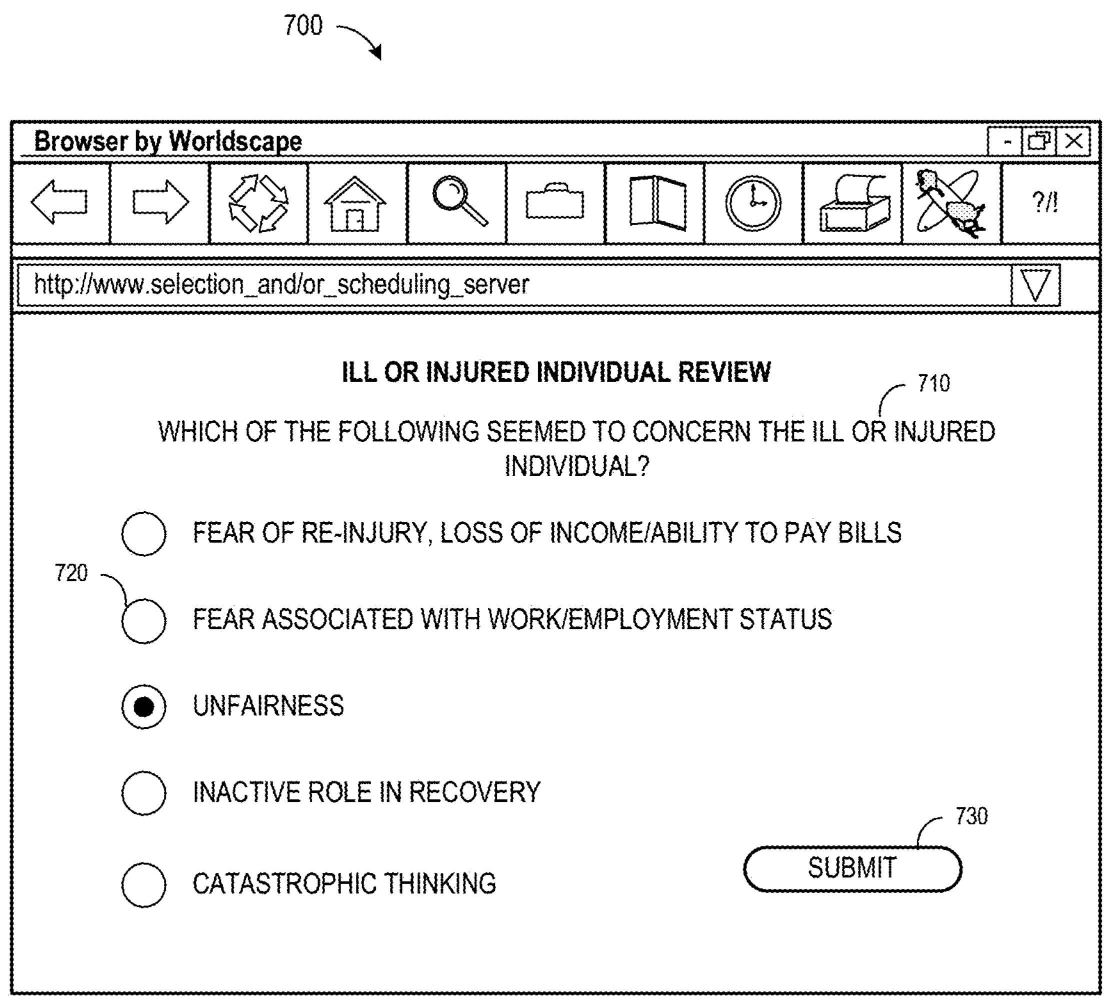
FIG. 7 is a graphical user interface of an ill or injured individual review display in accordance with some embodiments.

FIG. 7 is a graphical user interface of an ill or injured individual review display 700 in accordance with some embodiments. In particular, a nurse or recovery coach might use the display to answer questions 710 about the ill or injured individual (e.g., via graphical selections 720), such as questions about his or her fear of re-injury, fears associated with employment status or return to full function, unfairness, an inactive role in recovery, catastrophic thinking, etc.

In general, and for the purposes of introducing concepts of embodiments of the present invention, a computer system may be utilized to direct employees or vendors to conduct return-to-work or return-to-functional communications relating to insurance policies and/or to claims. Note that embodiments may be implemented via a computer system operated by an insurance company or third-party that may be associated with, for example, workers' compensation, automobile liability, and/or group benefits insurance policies.

The computer system may include a database storage module. In terms of its hardware the data storage module may be conventional, and may be composed, for example, by one or more magnetic hard disk drives. A function performed by the data storage module in the computer system is to receive, store and provide access to files relating to ill or injured individuals. The computer system may also include a distributed data communication network to which the data storage module is coupled. The data communication network may, for example, be conventional in its construction and functionality, and may serve as an "intranet" for the insurance company. In some embodiments, the data communication network may also incorporate and/or be connected to a public data communication network, such as the Internet.

The computer system may further include a number of terminals that may be employed by employees of the insurance company and/or a third party who are assigned to conduct communications in regard to the company's handling of insurance claims. As will be seen, the terminals may be constituted by conventional PCs coupled to the data communication network. One function that may be performed by the terminals is to communicate with ill or injured individuals' communication devices.

In addition, the computer system may include a data acquisition processor that is also coupled to the data communication network. The data acquisition processor may be constituted by one or more conventional microprocessors included in one or more server computers that may be programmed to function in accordance with the present invention. The data acquisition processor may function to receive information from the terminals (via the data communication network) and to store the data in the database storage module. The data acquisition processor may also classify the data source feedback responses as to whether the responses are satisfactory, unsatisfactory, indicative of data source loyalty, etc. The data acquisition processor may also generate alert messages to be sent to recovery coaches and/or team leaders and batches of electronic files to be transmitted on a periodic basis (e.g., daily basis).

Moreover, the computer system may include a workflow router that is coupled to the data communication network and thus is in communication, at least from time to time, with the data acquisition processor. The workflow router may be constituted by one or more conventional microprocessors that may for example be included in one or more conventional server computers. For example, the workflow router may at least partially overlap with the data acquisition processor. The workflow router may operate to route, to the terminals, communication links to ill or injured individuals. In some embodiments, the workflow router may also operate to capture and record actions taken by recovery coaches.

Figure 8:
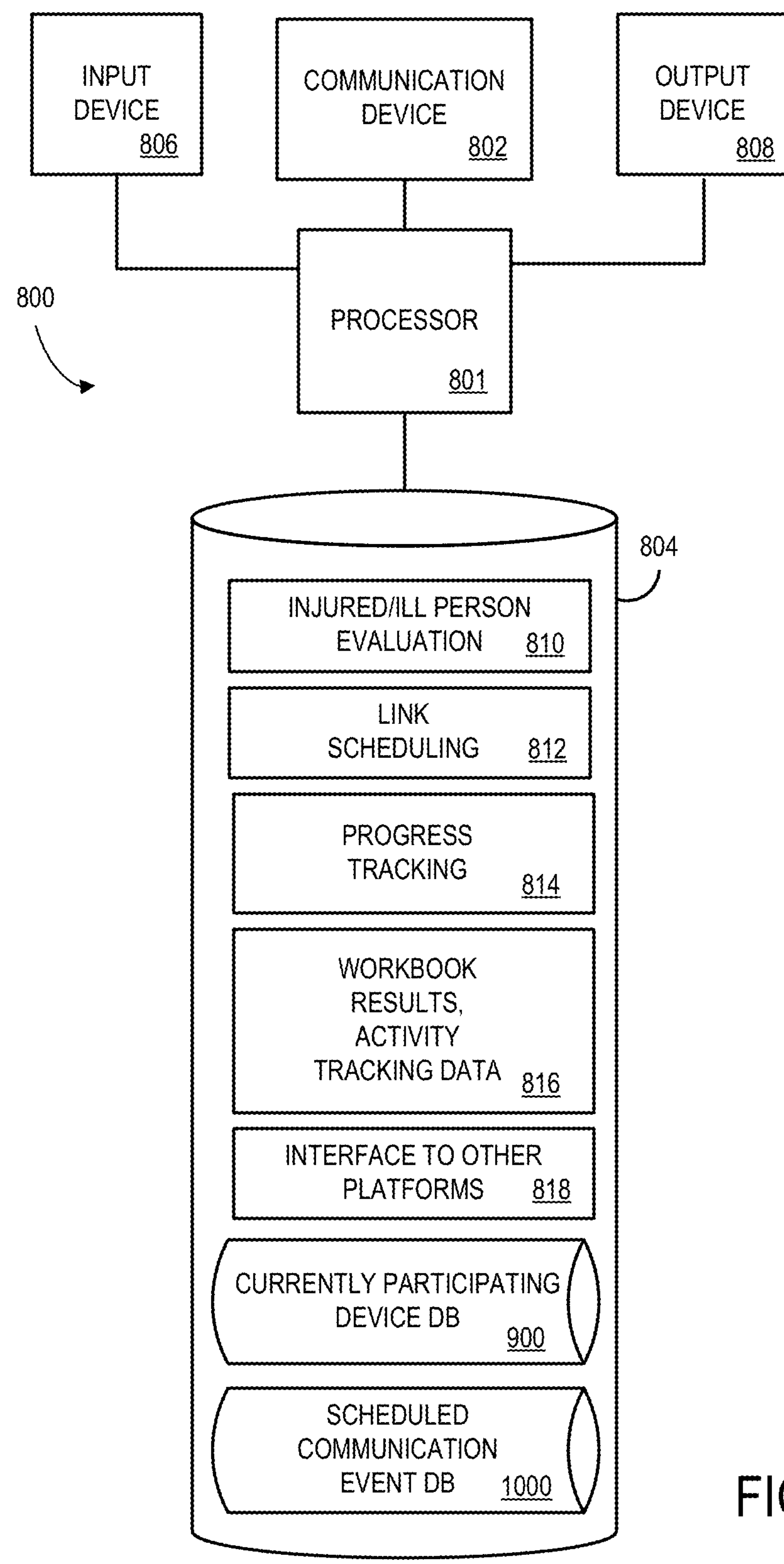
FIG. 8 is a block diagram that illustrates a recovery server or platform in accordance with some embodiments.

FIG. 8 is a block diagram that illustrates a recovery server 800. In its hardware aspects the recovery server 800 (such as a return to work or a return to function server) may be entirely conventional, but programmed to provide functionality as described herein.

As depicted, the recovery server 800 includes a computer processor 801 operatively coupled to a communication device 802, a storage device 804, an input device or devices 806 and an output device 808. The communication device 802 may be used to facilitate communication with, for example, other servers/terminals/PCs coupled to a distributed data communication network. The input device(s) 806 may comprise, for example, a keyboard, a keypad, a mouse or other pointing device, a microphone, knob or a switch, an Infra-Red ("IR") port, a docking station, and/or a touch screen. The input device(s) 806 may be used, for example, to enter information. Output device 808 may comprise, for example, a display (e.g., a display screen), a speaker, and/or a printer.

Storage device 804 may comprise any appropriate information storage device, including combinations of magnetic storage devices (e.g., magnetic tape and hard disk drives), optical storage devices, and/or semiconductor memory devices such as Random Access Memory ("RAM") devices and Read Only Memory ("ROM") devices.

The storage device 804 stores one or more programs or portions of programs (at least some of which being indicated by blocks 810 through 818) for controlling the processor 801. The processor 801 performs instructions of the programs, and thereby operates in accordance with the present invention. In some embodiments, the programs may include a program or program module 810 that programs the recovery server 800 to acquire data about ill or injured individuals to be evaluated.

Another program or program module stored on the storage device 804 is indicated at block 812 and is operative to allow the recovery server 800 to assign and manage communication links (e.g., telephone calls) with ill or injured individuals (e.g., on a weekly basis or other schedule).

Still another program or program module stored on the storage device 804 is indicated at block 814. The program (or program module) 814 may program the recovery server 800 to track the progress of the ill or injured individual's recovery. Such progress may be tracked, for example, based on the ill or injured individual's self-reported data (e.g., level of function experienced, number of minutes of activity performed etc.).

Another program/program module 816 programs the recovery server 800 to gather, receive, store and analyze workbook results (e.g., results entered by an ill or injured individual via a workbook smartphone application or other electronic application) and/or activity tracking data (e.g., number of steps walked each day).

A further program/program module 818 provides an interface between other program functions of the return to work server 800 and, for example, monitor devices, insurance policy databases, Human Resource ("HR") databased, etc. According to some embodiments, this program/program module 818 may further facilitate the generation of automatic alert signals based on data received from an ill or injured individual.

There may also be stored in the storage device 804 other software, such as one or more conventional operating systems, device drivers, communications software, database management software, etc.

Still further, various kinds of data needed for operation of the recovery server 800 may be stored in the storage device 804, including for example, a currently participating device database 900 and a scheduled communication database 1000 (including, in some embodiments, a recording of the claimants voice) automatically updated by the processor 801.

Referring to FIG. 9, a table is shown that represents a currently participating device database 900 (e.g., an ill or injured individual database) that may be stored at a scheduling server, tool, or platform according to some embodiments. The table may include, for example, entries that may be associated with individuals who have missed work due to an injury or illness. The table may also define fields 902, 904, 906, 908, 910 for each of the entries. The fields 902, 904, 906, 908, 910 may, according to some embodiments, specify: an injured/ill person identifier 902, a communication address or identifier 904, a current week 906, a current level of function 908, and a link status 910. The currently participating device database 900 may be created and updated, for example, as information is received from a selection server, a disabled individual, a monitoring device, etc.

The injured/ill person identifier 902 may be, for example, a unique alphanumeric code identifying a worker who is not at work or non-fully functional due to an injury or illness. The communication address or identifier 904 may be, for example, a telephone number, email address, etc. that may be used to contact the individual. The current week 906 might indicate his or her current progress through an intervention program (e.g., he or she is currently in week 3 of a 10 week program). The current level of function 908 might track how the individual is functioning (e.g., on a scale from 1 through 10) and the link status 910 might indicate that this week's communication is pending, has been re-scheduled, has been completed, etc.

Referring to FIG. 10, a table is shown that represents a scheduled communication event database 1000 (e.g., a scheduled communication event or telephone call database) that may be stored at a scheduling server, tool, or platform according to some embodiments. The table may include, for example, entries that may be associated with ill or injured individuals who are not at work or non-fully functional due to an injury or illness. The table may also define fields 1002, 1004, 1006, 1008, 1010 for each of the entries. The fields 1002, 1004, 1006, 1008, 1010 may, according to some embodiments, specify: an ill or injured individual identifier 1002, a communication address or identifier 1004, a currently scheduled communication 1006, a next scheduled communication 1008, and physical delivery 1010. The scheduled communication event database 1000 may be created and updated, for example, as information is received from a scheduling server, an ill or injured individual, a monitoring device, fulfillment center, etc.

The ill or injured individual identifier 1002 may be, for example, a unique alphanumeric code identifying an ill or injured individual who is not at work or non-fully functional due to an injury or illness and may be based on or associated with the injured/ill person identifier 902 in the currently participating device database 900. The communication address or identifier 1004 may be, for example, a telephone number, email address, etc. that may be used to contact the ill or injured individual and may be based on or associated with the communication identifier 904 in the currently participating device database 900. The currently scheduled communication 1006 might, for example, indicate when a recovery coach will call the ill or injured individual (e.g., a date and time). The next scheduled communication 1008 might indicate the next communication link that is scheduled (e.g., and may be, for example, one week after the currently scheduled communication 1006). The delivery 1010 might indicate a workbook, letter, or package that will be delivered to the disabled individual by postal mail/electronic means in connection with the currently scheduled communication 1006 or the next scheduled communication 1008.

Thus, embodiments may let a selection server facilitate assistance by looking for one or more "yellow flags" that might be associated with behavioral risk factors that may trigger the insurance company to identify and/or intervene to help an ill or injured individual. Note that a recovery coach might not ask about pain, but instead focus on function (instead of pain): such as by asking "What have you been doing this week?" By directing the ill or injured individual to think about function instead of pain, his or her recovery may be improved. The recovery coach might ask an ill or injured individual, for example, to rate his or her level of function on a scale from 0 to 10 (with 0 being in a coma and 10 being an ability to do everything he or she would like to do). Note that a recovery coach may avoid answering claim or clinical questions (the coach might not verify payment schedule, compensability questions, Utilization Review ("UR") decisions, medical treatment/appointments, Durable Medical Equipment ("DME") issues, pharmacy issues, etc.). Coaches may also avoid providing opinions regarding medical treatment, providers, claim handler/Nurse Care Manager ("NCM") performance, jurisdictional questions, etc. Instead, the recovery coach may focus on weekly topics (stress or anger management), progress, scheduling issues, issues with toolkits and/or workbook, coach performance, etc.

According to some embodiments, specific claim file attributes may be used by a selection server to identify ill or injured individuals who may be candidates for an intervention program. Such attributes might include, for example, a jurisdiction (e.g., a case is covered by New Jersey workers' compensation regulations), an amount of lost time (e.g., out of work at least 21 days), a lack of planned clinical intervention (e.g., surgery), an ill or injured worker investigation has been completed, whether the injured worker speaks English or some other language, whether the ill or injured individual's attorney approval may be required, whether or not one or more psychosocial risk factors are present, etc.

When gathering information, a claim handler, analyst, or other party might capture important risk factors in the course of interaction with a claimant. For example, the claim handler might note yellow flags. Similarly, a triage consultant or clinician might document yellow flags. A coach or team leader may then review the gathered material to determine if the ill or injured individual should participate in the program. The yellow flags might include a claim handler, analyst, or other party noting that an ill or injured individual has expressed one or more of the following: an expected return to work of greater than 10 days, a fear of re-injury, activity, loss of income/ability to pay bills, fear associated with work/employment status, a perception of injustice, an inactive role in recovery, catastrophic thinking, anger, sleep concerns, and/or stress.

When enrolled, an ill or injured individual may receive an introductory or interim toolkit that may include materials such as a sleep mask, a stress ball, and a workbook. The workbook might be associated with weekly topics, such as: the individual's story, the individual's future, recovering at work, the individual's pain, the individual's activity, stress, sleep, thinking, anger, flare-ups, activity tracking, thought tracking, etc. Upon program completion, the ill or injured individual may receive materials, such as a graduation certificate, a visor/baseball cap, and/or other materials.

According to some embodiments, an ill or injured individual may be subject to a risk assessment score (e.g., during weeks 1, 5, and 10 of a 10 week program). The scores may, for example, be included in a coach report and may reflect either a high risk category or a low risk category. Some examples of risk assessment issues may include indications that an ill or injured individual has: pain that has spread in the last two weeks, only walked short distances because of the injury, dressed more slowly than usual, felt that his or her pain is terrible and is never going to improve, not enjoyed the things he or she used to enjoy, etc.

According to some embodiments, the system may electronically store records associated with an ill or injured individual. For example, the following "internal only" file notes might be viewable by claim staff: telephone calls (attended, attempted, and/or rescheduled calls), an initial report, an interim report, a final report and/or discharge notes, roundtable findings, distribution of kits, sentinel events, discrepancies in mechanism of injury, significant clinical changes, surgery, new injuries, changes in diagnosis or condition, whether the disabled individual's attorney approval may be required, a return to work, availability, existence of a second job, claim settlement, etc.

Figure 11:
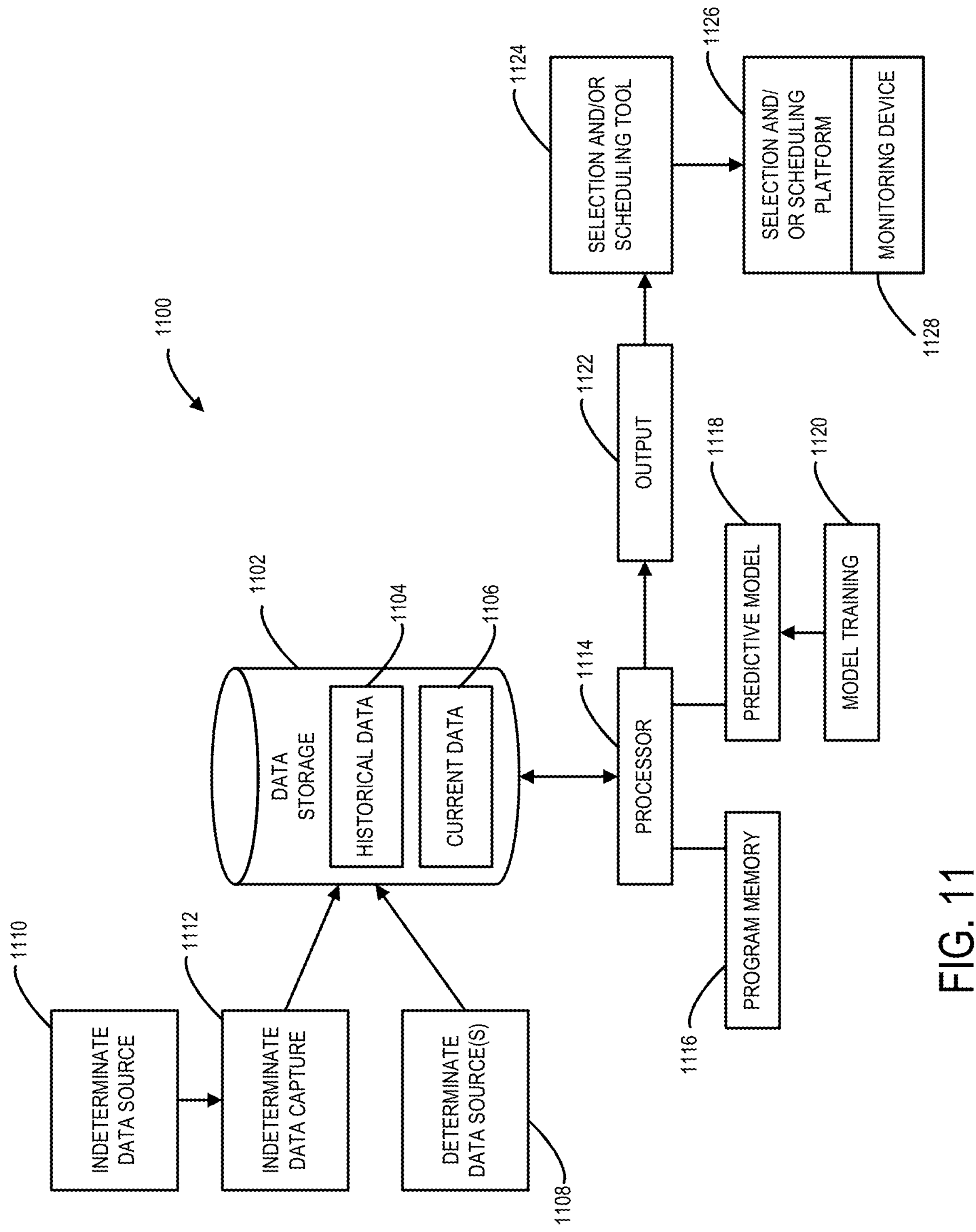
FIG. 11 illustrates a system that may be associated with a predictive model according to some embodiments.

According to some embodiments, one or more predictive models may be used to select ill or injured individuals for program participation and/or to schedule communications with ill or injured individuals. Features of some embodiments associated with a predictive model will now be described by first referring to FIG. 11. FIG. 11 is a partially functional block diagram that illustrates aspects of a computer system 1100 provided in accordance with some embodiments of the invention. For present purposes it will be assumed that the computer system 1100 is operated by an insurance company (not separately shown) for the purpose of supporting automated selections and scheduling indications.

The computer system 1100 includes a data storage module 1102. In terms of its hardware the data storage module 1102 may be conventional, and may be composed, for example, by one or more magnetic hard disk drives. A function performed by the data storage module 1102 in the computer system 1100 is to receive, store and provide access to both historical transaction data (reference numeral 1104) and current transaction data (reference numeral 1106). As described in more detail below, the historical transaction data 1104 is employed to train a predictive model to provide an output that indicates a recommendation of acceptance of ill or injured individuals, and the current transaction data 1106 is thereafter analyzed by the predictive model. Moreover, as time goes by, and results become known from processing current transactions, at least some of the current transactions may be used to perform further training of the predictive model. Consequently, the predictive model may thereby adapt itself to changing recommendation results.

Either the historical transaction data 1104 or the current transaction data 1106 might include, according to some embodiments, determinate and indeterminate data. As used herein and in the appended claims, "determinate data" refers to verifiable facts such as the an age of a home; an automobile type; a policy date or other date; a driver age; a time of day; a day of the week; a geographic location, address or ZIP code; and a policy number.

As used herein, "indeterminate data" refers to data or other information that is not in a predetermined format and/or location in a data record or data form. Examples of indeterminate data include narrative speech or text, information in descriptive notes fields and signal characteristics in audible voice data files (e.g., which might be associated with identifying one or more "yellow flags").

The determinate data may come from one or more determinate data sources 1108 that are included in the computer system 1100 and are coupled to the data storage module 1102. The determinate data may include "hard" data like a claimant's name, date of birth, social security number, type of injury, job title, policy number, address, etc. One possible source of the determinate data may be the insurance company's policy database and/or employer's HR database (not separately indicated).

The indeterminate data may originate from one or more indeterminate data sources 1110, and may be extracted from raw files or the like by one or more indeterminate data capture modules 1112. Both the indeterminate data source(s) 1110 and the indeterminate data capture module(s) 1112 may be included in the computer system 1100 and coupled directly or indirectly to the data storage module 1102. Examples of the indeterminate data source(s) 1110 may include data storage facilities for document images, for text files, and digitized recorded voice files. Examples of the indeterminate data capture module(s) 1112 may include one or more optical character readers, a speech recognition device (i.e., speech-to-text conversion), a computer or computers programmed to perform natural language processing, a computer or computers programmed to identify and extract information from narrative text files, a computer or computers programmed to detect key words in text files, and a computer or computers programmed to detect indeterminate data regarding an individual.

The computer system 1100 also may include a computer processor 1114. The computer processor 1114 may include one or more conventional microprocessors and may operate to execute programmed instructions to provide functionality as described herein. Among other functions, the computer processor 1114 may store and retrieve historical insurance transaction data 1104 and current transaction data 1106 in and from the data storage module 1102. Thus the computer processor 1114 may be coupled to the data storage module 1102.

The computer system 1100 may further include a program memory 1116 that is coupled to the computer processor 1114. The program memory 1116 may include one or more fixed storage devices, such as one or more hard disk drives, and one or more volatile storage devices, such as RAM devices. The program memory 1116 may be at least partially integrated with the data storage module 1102. The program memory 1116 may store one or more application programs, an operating system, device drivers, etc., all of which may contain program instruction steps for execution by the computer processor 1114.

The computer system 1100 further includes a predictive model component 1118. In certain practical embodiments of the computer system 1100, the predictive model component 1118 may effectively be implemented via the computer processor 1114, one or more application programs stored in the program memory 1116, and computer stored as a result of training operations based on the historical transaction data 1104 (and possibly also data received from a third party). In some embodiments, data arising from model training may be stored in the data storage module 1102, or in a separate computer store (not separately shown). A function of the predictive model component 1118 may be to determine appropriate recommendations of participation in a recovery program for ill or injured individuals (or how communications with ill or injured individuals should be scheduled). The predictive model component may be directly or indirectly coupled to the data storage module 1102.

The predictive model component 1118 may operate generally in accordance with conventional principles for predictive models, except, as noted herein, for at least some of the types of data to which the predictive model component is applied. Those who are skilled in the art are generally familiar with programming of predictive models. It is within the abilities of those who are skilled in the art, if guided by the teachings of this disclosure, to program a predictive model to operate as described herein.

Still further, the computer system 1100 includes a model training component 1120. The model training component 1120 may be coupled to the computer processor 1114 (directly or indirectly) and may have the function of training the predictive model component 1118 based on the historical transaction data 1104 and/or information about potential insureds. (As will be understood from previous discussion, the model training component 1120 may further train the predictive model component 1118 as further relevant data becomes available.) The model training component 1120 may be embodied at least in part by the computer processor 1114 and one or more application programs stored in the program memory 1116. Thus the training of the predictive model component 1118 by the model training component 1120 may occur in accordance with program instructions stored in the program memory 1116 and executed by the computer processor 1114.

In addition, the computer system 1100 may include an output device 1122. The output device 1122 may be coupled to the computer processor 1114. A function of the output device 1122 may be to provide an output that is indicative of (as determined by the trained predictive model component 1118) particular recommendations. The output may be generated by the computer processor 1114 in accordance with program instructions stored in the program memory 1116 and executed by the computer processor 1114. More specifically, the output may be generated by the computer processor 1114 in response to applying the data for the current ill or injured individual to the trained predictive model component 1118. The output may, for example, be a "yes" or "no" indication or a numerical rating. In some embodiments, the output device 1122 may be implemented by a suitable program or program module executed by the computer processor 1114 in response to operation of the predictive model component 1118.

Still further, the computer system 1100 may include a selection and/or scheduling tool or module 1124. The selection and/or scheduling tool or module 1124 may be implemented in some embodiments by a software module executed by the computer processor 1114. The selection and/or scheduling tool or module 1124 may have the function of rendering a portion of the display on the output device 1122. Thus the selection and/or scheduling tool or module 1124 may be coupled, at least functionally, to the output device 1122. In some embodiments, for example, the selection and/or scheduling tool or module 1124 may direct workflow by referring, to a selection and/or scheduling platform 1126, current recommendation results generated by the predictive model component 1118 and found to be associated with various results or scores. In some embodiments, these recommendations may be provided to monitoring 1128 that may be used by a return to work coach to talk with injured workers.

Figure 12:
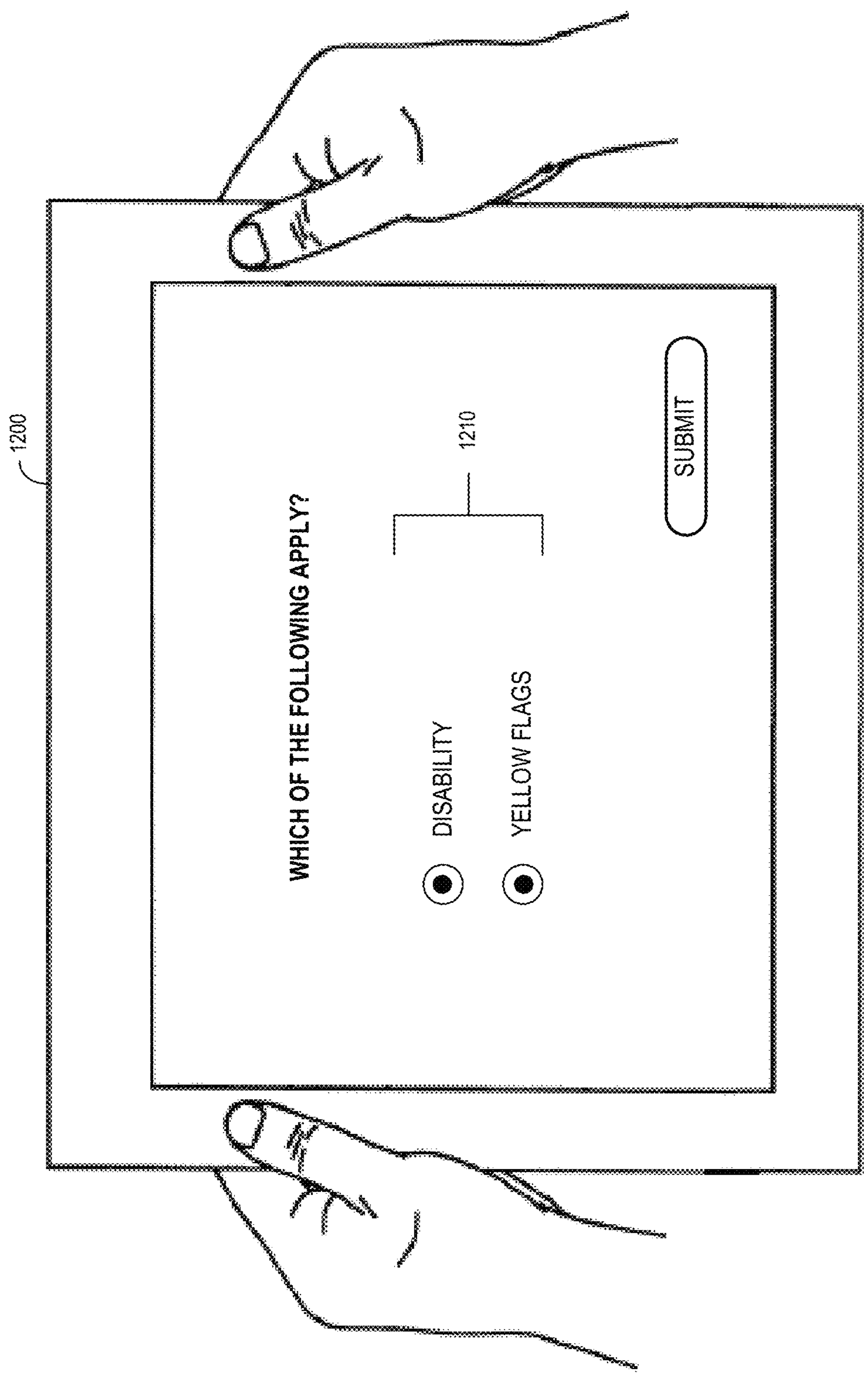
FIG. 12 is display illustrating a portion of a monitoring device interface that might be provided via a tablet computer or other such electronic device in accordance with any of the embodiments described herein.

Although specific hardware and data configurations have been described herein, note that any number of other configurations may be provided in accordance with embodiments of the present invention (e.g., some of the information associated with the databases described herein may be combined or stored in external systems). Additionally, one or more of the elements described herein may be practiced in a distributed cloud computing environment where tasks are performed by logically or physically remote processing devices that are linked through one or more communications networks. For example, FIG. 12 illustrates a handheld tablet 1200 injured worker selection display according to some embodiments described herein. In particular, the handheld tablet 1200 is displaying a set of factors 1210 that might be selected and then used to determine whether or not a particular ill or injured individual should particulate in a recovery program.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A computer-implemented method, comprising:

automatically generating, by a predictive model component, a selection algorithm to indicate that a worker associated with a communication address has been in a second state for at least a threshold period of time and that the worker associated with the communication address exhibits a set of behavioral characteristics;

accessing, by a selection server, information in a potential communication device database, the potential communication device database storing information about a plurality of communication addresses associated with workers, of an employer, who transition from a first state to the second state as a result of a work-related physical injury;

automatically identifying, by the selection server, a communication address, associated with an identified worker, as meeting the selection algorithm generated by the predictive model component;

copying, by the selection server, information about the identified communication address from the potential communication device database to a currently participating device database;

measuring, by an activity tracking device, movement data and sleep quality of the identified worker;

transmitting the movement data and sleep quality from the activity tracking device to the identified communication address to facilitate a detection by a software application that the identified worker has transitioned from the second state back to the first state;

automatically scheduling, by a scheduling server of an insurer providing workers' compensation benefits for the employer, a series of communication events between a monitoring device and the identified communication address via a distributed communication network;

arranging, by the scheduling server, for a communication link to be established in accordance with each of the scheduled series of communication events until the transition from the second state back to the first state is detected for the identified worker; and transmitting information about the identified communication address, the automatically scheduled series of communication events, the movement data and sleep quality measured by the activity tracking device, the work-related physical injury, at least one workers' compensation insurance claim, and the transition from the from the second state back to the first state to the predictive model component to improve the selection algorithm.

2. The method of claim 1, wherein the identified communication address is associated with at least one of: a telephone, a personal computer, a smartphone, a smartwatch, a tablet computer, and a chat interface.

3. The method of claim 2, further comprising:

automatically arranging for a physical item to be delivered to a postal address in connection with at least some of the scheduled series of communication events.

4. The method of claim 3, wherein the scheduling server automatically arranges for a physical workbook to be delivered in connection with a first of the scheduled series of communication events.

5. The method of claim 3, wherein the physical item is associated with at least one of: an activity tracking device, a water bottle, a wrist band, a stress ball, a sleeping mask, a cap or visor, training media, and a certificate of completion.

6. The method of claim 2, wherein the identified communication address is associated with an ill or injured worker, the first state is associated with an "at work" or "fully functional" status, and the second state is associated with a "not at work" or "non-fully functional" status.

7. The method of claim 6, wherein at least one intermediate state exists between the "at work" or "fully functional" and "not at work" or "non-fully functional" states, including a "modified work duty" or "partially functional" state.

8. The method of claim 6, wherein the monitoring device is associated with a recovery coach to encourage at least one of: physical activity, social activity, and cognitive activity.

9. A non-transitory, computer-readable medium storing instructions, that, when executed by a computer processor, cause the computer processor to perform a method comprising:

automatically generating, by a predictive model component, a selection algorithm to indicate that a worker associated with a communication address has been in a second state for at least a threshold period of time and that the worker associated with the communication address exhibits a set of behavioral characteristics;

accessing, by a selection server, information in a potential communication device database, the potential communication device database storing information about a plurality of communication addresses associated with workers, of an employer, who transition from a first state to the second state as a result of a work-related physical injury;

automatically identifying, by the selection server, a communication address, associated with an identified worker, as meeting the selection algorithm generated by the predictive model component;

copying, by the selection server, information about the identified communication address from the potential communication device database to a currently participating device database;

measuring, by an activity tracking device, movement data and sleep quality of the identified worker;

transmitting the movement data and sleep quality from the activity tracking device to the identified communication address to facilitate a detection by a software application that the identified worker has transitioned from the second state back to the first state;

automatically scheduling, by a scheduling server of an insurer providing workers' compensation benefits for the employer, a series of communication events between a monitoring device and the identified communication address via a distributed communication network;

arranging, by the scheduling server, for a communication link to be established in accordance with each of the scheduled series of communication events until the transition from the second state back to the first state is detected for the identified worker; and transmitting information about the identified communication address, the automatically scheduled series of communication events, the movement data and sleep quality measured by the activity tracking device, the work-related physical injury, at least one workers' compensation insurance claim, and the transition from the from the second state back to the first state to the predictive model component to improve the selection algorithm.

10. The medium of claim 9, wherein the identified communication address is associated with an ill or injured worker, the first state is associated with an "at work" or "fully functional" status, and the second state is associated with a "not at work" or "non-fully functional" status.

11. The medium of claim 10, wherein at least one intermediate state exists between the "at work" or "fully functional" and "not at work" or "non-fully functional" states, including a "modified work duty" or "partially functional" state.

12. The medium of claim 10, wherein the monitoring device is associated with a recovery coach to encourage at least one of: physical activity, social activity, and cognitive activity.

13. The medium of claim 10, wherein the software application executing at the identified communication address is associated with at least one of:

workbook materials, training media, activity tracking features, and goal tracking functionality.

14. The medium of claim 13, wherein information measured by the activity tracking device and information about an ill or injured worker's activity are accessible by the ill or injured worker and the recovery coach via a web portal.

15. The medium of claim 10, wherein the selection algorithm is further based on at least one of: a geographic location, a type of injury, whether an ill or injured worker's attorney approval is required, a language spoken, and a risk score.

16. The medium of claim 15, wherein the set of behavioral characteristics includes at least one of: an expectation, a belief, catastrophic thinking, fear, perceived injustice, passivity, a lack of coping skills, unfairness, anger, sleep issues, and stress.

17. A system, comprising:

(a) a potential communication device database storing information about a plurality of communication addresses associated with workers, of an employer, who transition from a first state to a second state as a result of a work-related physical injury;

(b) a currently participating device database;

(c) a predictive model component to automatically generate a selection algorithm indicating that the communication address is associated with a worker who has been in the second state for at least a threshold period of time and that the worker associated with the communication address exhibits a set of behavioral characteristics;

(d) a selection server, in communication with the potential communication device database and the currently participating device database, programmed to:

(i) access information in the potential communication database, (ii) automatically identify a communication address, associated with an identified worker, as meeting the selection algorithm generated by the predictive model component, and (iii) copy information about the identified communication address from the potential communication device database to the currently participating device database;

(e) an activity tracking device to measure movement data and sleep quality of the identified worker and transmit the movement data and sleep quality to the identified communication address to facilitate a detection by a software application that the identified worker has transitioned from the second state back to the first state; and (f) a scheduling server of an insurer providing workers' compensation benefits for the employer and coupled to the currently participating device database, programmed to:

(iv) automatically schedule a series of communication events between a monitoring device and the identified communication address via a distributed communication network, and (v) arrange for a communication link to be established in accordance with each of the scheduled series of communication events until the transition from the second state back to the first state is detected for the identified worker;

wherein information about the identified communication address, the automatically scheduled series of communication events, the movement data and sleep quality measured by the activity tracking device, the work-related physical injury, at least one workers' compensation insurance claim, and the transition from the from the second state back to the first state are all transmitted to the predictive model component to improve the selection algorithm.

18. The system of claim 17, wherein the distributed communication network is associated with at least one of a public switched telephone network, the Internet, and a web portal.

19. The system of claim 17, wherein the identified communication address is associated with at least one of: a telephone, a personal computer, a smartphone, a smartwatch, a tablet computer, and a chat interface.

20. The system of claim 17, wherein the scheduling server is further programmed to:

(vi) automatically arrange for a physical item to be delivered to a postal address associated with the communication address in connection with at least some of the scheduled series of communication events.

21. The system of claim 20, wherein the scheduling server automatically arranges for a physical workbook to be delivered in connection with a first of the scheduled series of communication events.

22. The system of claim 20, wherein at least one physical item is associated with at least one of: an activity tracking device, a water bottle, a wrist band, a stress ball, a sleeping mask, a cap or visor, training media, and a certificate of completion.

23. The system of claim 19, wherein the identified communication address is associated with an ill or injured worker, the first state is associated with an "at work" or "fully functional" status, and the second state is associated with a "not at work" or "non-fully functional" status.

24. The system of claim 23, wherein at least one intermediate state exists between the "at work" or "fully functional" and "not at work" or "non-fully functional" states, including a "modified work duty" or "partially functional" state.

* * * * *